(12) United States Patent
Beck et al.

(10) Patent No.: US 7,787,684 B2
(45) Date of Patent: Aug. 31, 2010

(54) METHOD FOR PLANNING AN EXAMINATION IN A MAGNETIC RESONANCE SYSTEM

(75) Inventors: Walter Beck, Erlangen (DE); Klaus Mayer, Eckental (DE); Cecile Mohr, Erlangen (DE); Jochen Zeltner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1063 days.

(21) Appl. No.: 11/499,277

(22) Filed: Aug. 3, 2006

(65) Prior Publication Data

US 2007/0036413 A1 Feb. 15, 2007

(30) Foreign Application Priority Data

Aug. 3, 2005 (DE) .................. 10 2005 036 515

(51) Int. Cl.
*G06K 9/00* (2006.01)
*G06K 9/36* (2006.01)
*A61B 5/05* (2006.01)

(52) U.S. Cl. .................. 382/131; 382/128; 382/284; 600/410; 128/916; 128/920

(58) Field of Classification Search ......... 382/128–133, 382/154, 284; 324/309, 300; 600/409–411, 600/413, 415, 300; 707/13, 130, 201; 128/906, 128/916, 920
See application file for complete search history.

(56) References Cited

U.S. PATENT DOCUMENTS

| | | | | |
|---|---|---|---|---|
| 5,501,218 A * | 3/1996 | Usui | ............. | 600/410 |
| 5,539,312 A * | 7/1996 | Fu et al. | ............. | 324/309 |
| 5,997,883 A * | 12/1999 | Epstein et al. | ............. | 324/306 |
| 6,055,326 A * | 4/2000 | Chang et al. | ............. | 382/132 |
| 6,195,409 B1 * | 2/2001 | Chang et al. | ............. | 378/20 |
| 6,292,684 B1 * | 9/2001 | Du et al. | ............. | 600/410 |
| 6,363,163 B1 * | 3/2002 | Xu et al. | ............. | 382/130 |
| 6,437,571 B1 * | 8/2002 | Danby et al. | ............. | 324/322 |
| 6,511,426 B1 * | 1/2003 | Hossack et al. | ............. | 600/437 |
| 6,529,762 B1 * | 3/2003 | Ladebeck | ............. | 600/410 |
| 6,580,937 B2 * | 6/2003 | Ho et al. | ............. | 600/415 |
| 6,584,337 B2 * | 6/2003 | Dumoulin et al. | ............. | 600/410 |
| 6,611,702 B2 * | 8/2003 | Rohling et al. | ............. | 600/415 |

(Continued)

FOREIGN PATENT DOCUMENTS

DE 103 46 410 A1 5/2005

(Continued)

*Primary Examiner*—Matthew C Bella
*Assistant Examiner*—Mia M Thomas
(74) *Attorney, Agent, or Firm*—Schiff Hardin LLP

(57) ABSTRACT

In a method for planning an examination of an examination subject in a magnetic resonance system, the planning of the examination ensues based on a composite overview image that is composed of at least two individual images. A first part of the overview image is acquired and the first part of the overview image is made available to operating personnel of the magnetic resonance system for planning further measurements. A second part of the overview image is acquired and the first part and the second part of the overview image are combined. The combined image of the first part and second part of the overview image is made available for planning further measurements. The first part of the overview image is made available to operating personnel no later than before making the overview image available.

9 Claims, 3 Drawing Sheets

U.S. PATENT DOCUMENTS

| | | | |
|---|---|---|---|
| 6,678,703 B2* | 1/2004 | Rothschild et al. | 707/201 |
| 6,897,655 B2* | 5/2005 | Brittain et al. | 324/309 |
| 6,898,302 B1* | 5/2005 | Brummer | 382/131 |
| 6,979,124 B2* | 12/2005 | Gerwin et al. | 378/207 |
| 7,072,497 B2* | 7/2006 | Faber et al. | 382/128 |
| 7,167,581 B2* | 1/2007 | Kawano | 382/128 |
| 7,245,749 B2* | 7/2007 | Okuzawa | 382/128 |
| 7,312,610 B2* | 12/2007 | Harder | 324/307 |
| 7,466,849 B2* | 12/2008 | Haider et al. | 382/128 |
| 7,467,006 B2* | 12/2008 | Abe et al. | 600/420 |
| 7,480,526 B2* | 1/2009 | Mayer et al. | 600/410 |
| 7,536,042 B2* | 5/2009 | Murphy et al. | 382/128 |
| 7,656,155 B2* | 2/2010 | Tatebayashi | 324/307 |
| 7,693,563 B2* | 4/2010 | Suresh et al. | 600/407 |
| 2002/0042566 A1* | 4/2002 | Matsuzaki et al. | 600/407 |
| 2002/0071599 A1* | 6/2002 | Herget et al. | 382/131 |
| 2002/0097901 A1* | 7/2002 | Xu et al. | 382/131 |
| 2002/0151786 A1* | 10/2002 | Shukla et al. | 600/411 |
| 2002/0173715 A1* | 11/2002 | Kruger et al. | 600/410 |
| 2002/0198447 A1* | 12/2002 | Van Muiswinkel et al. | 600/410 |
| 2003/0036693 A1* | 2/2003 | Avinash et al. | 600/413 |
| 2003/0144589 A1* | 7/2003 | Roell | 600/410 |
| 2003/0178995 A1* | 9/2003 | Peshkovsky et al. | 324/307 |
| 2004/0015070 A1* | 1/2004 | Liang et al. | 600/407 |
| 2004/0254454 A1* | 12/2004 | Kockro | 600/424 |
| 2005/0154292 A1* | 7/2005 | Tank | 600/410 |
| 2005/0187459 A1* | 8/2005 | Trequattrini et al. | 600/415 |
| 2005/0265516 A1* | 12/2005 | Haider | 378/20 |
| 2006/0056674 A1* | 3/2006 | Lehtonen-Krause | 382/131 |
| 2007/0016002 A1* | 1/2007 | Mayer et al. | 600/410 |
| 2007/0036413 A1* | 2/2007 | Beck et al. | 382/128 |
| 2007/0161889 A1* | 7/2007 | Mayer et al. | 600/410 |
| 2007/0173716 A1* | 7/2007 | Mayer et al. | 600/410 |
| 2007/0210793 A1* | 9/2007 | Kiefer | 324/307 |
| 2008/0009709 A1* | 1/2008 | Guehring et al. | 600/414 |
| 2008/0015430 A1* | 1/2008 | Takamori | 600/415 |
| 2008/0205725 A1* | 8/2008 | Schmitt et al. | 382/130 |
| 2008/0212858 A1* | 9/2008 | Boese et al. | 382/130 |
| 2008/0279433 A1* | 11/2008 | Brau et al. | 382/131 |
| 2009/0048505 A1* | 2/2009 | Kuth et al. | 600/410 |
| 2009/0080749 A1* | 3/2009 | Visser et al. | 382/131 |
| 2009/0110256 A1* | 4/2009 | Thielemans et al. | 382/131 |

FOREIGN PATENT DOCUMENTS

WO    WO2005033726 A1 * 10/2004

* cited by examiner

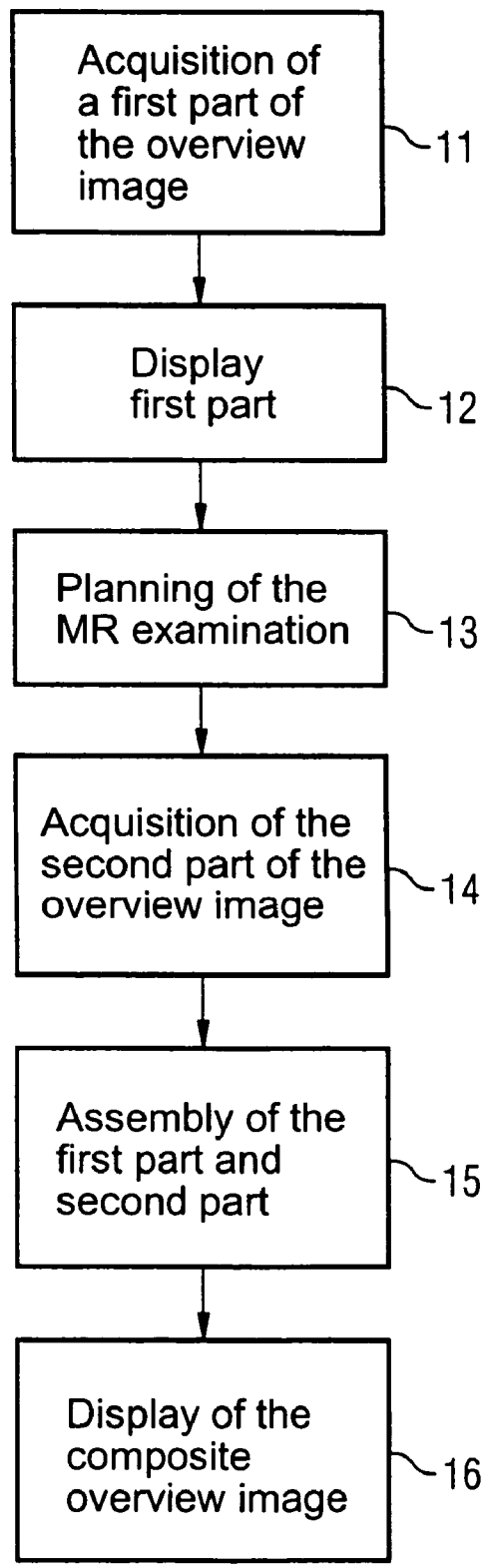

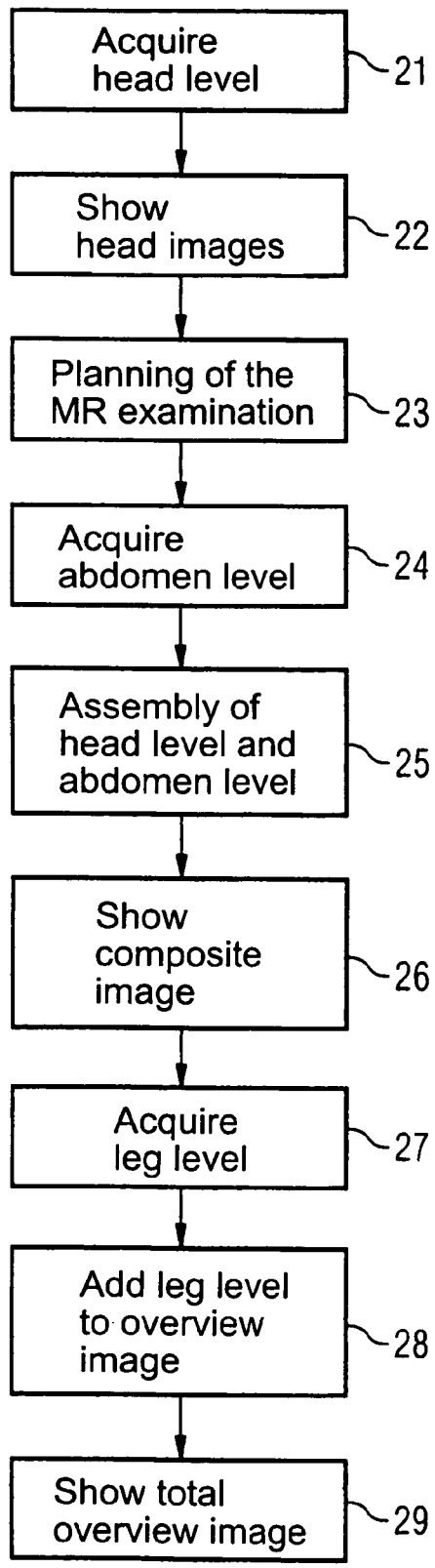

METHOD FOR PLANNING AN EXAMINATION IN A MAGNETIC RESONANCE SYSTEM

BACKGROUND OF THE INVENTION

1. Field of the Invention

The present invention concerns a method for planning an examination of an examination subject in a magnetic resonance system (MR system), of the type wherein the planning of the examination ensues based on a composite overview image that was assembled from at least two individual images. The present invention is, however, not exclusively for persons for whom a larger body region should be represented by MR images.

2. Description of the Prior Art

Imaging by means of magnetic resonance has increasingly proven to be indispensable for the diagnosis of various pathologies. In magnetic resonance systems used for such imaging, the trend has recently emerged that ever shorter magnet configurations are used for generation of the polarization (basic) field B0. These short magnet configurations help to reduce the claustrophobia that is typical for the examined person in closed magnet configurations since (dependent on the examined body part) the head projects out of such shorter magnets.

These shorter magnets, however, lead to the situation that the available field of view in the acquisition becomes ever smaller, such that it becomes more difficult to cover larger examination regions with only one examination (scan).

Furthermore, MR techniques have been developed with which a larger examination region can be examined, by the table on which the examined person rests being moved through the magnet, with MR images being acquired at successive table positions. The MR images acquired at the successive table positions are then assembled into an overall image.

Furthermore, an overview measurement typically ensues at the beginning in the examination, with the further progression of the examination being planned using the overview image by the position of the imaging slices and, if applicable, the parameters of the imaging being determined using the overview image. A number of overview measurements are conducted in the planning of an examination of a larger body region. The body regions to be examined, for example the head, abdomen and legs, are thereby measured in individual levels. After the end of the last level, the resulting images of the individual levels are combined. The image of the body thereby created is provided to the user for planning of the slices for the further measurements.

DE 103 46 410 A1 describes a method that enables a standardized description of the patient-related position and orientation of exposures in a magnetic resonance system, wherein a parameterized, anatomical body model is individualized by initial MR overview exposures of the patient, and patient-related information regarding the individualized model is determined from the relative position of the subsequent diagnostic slice image exposures for the position and orientation of the slice image exposures.

DE 103 57 203 A1 describes a method for representation of images in a magnetic resonance system, wherein an anatomical standard model is selected, the geometry of which is variable for an examination subject to be examined dependent on a diagnostic question. A number of overview images are subsequently acquired, and the image parameters are established dependent on the selected anatomical standard model.

According to the prior art, for a whole-body overview measurement, the image composition is activated only upon the ending of the measurement for the last level. The result images of the measurements of all individual levels are then assembled into a whole-body resulting image using an algorithm. The combined resulting images are provided to the user for planning the further examination. For planning an examination of a large body region, the user thus must wait until the last level is measured and the output image has been created. The user thus can begin the planning for measurements of the head level only when the overview measurement has been completely concluded and the resulting images of the overview images exist. This slows the entire examination and increases the time duration of the overall examination since the planning of the actual measurement can be begun only very late, which increases the cost of the examination.

SUMMARY OF THE INVENTION

An object of the present invention is to provide a method with which the planning of an examination can be accelerated when the examination is planned with an overview image that is composed of at least two individual images.

This object is achieved by a method according to the invention wherein a first part of the overview image is acquired in a first step and in a further step, the first part of the overview image is provided to the user or the operating personnel of the magnetic resonance system so that the user or operating personnel can plan further measurements using the first part of the overview image. A further, second part of the overview image is likewise acquired. This second part of the overview image is then combined with the first part of the overview image, and the combination of he first and second parts of the overview image is subsequently provided (i.e. is displayed) for planning further measurements (scans). According to the invention, after conclusion of the first part of the overview image, this is now immediately made available and displayed before the measurement of the second part of the imaging unit has ended and both parts have been combined with one another. This achieves a fast availability of the images generated in the individual levels such that the planning of an examination can already begin even though the overview measurement has not yet concluded, since the overview image embodies at least two different images that must be combined. Waiting until the end of the overview measurement for the result images is not necessary, such that a notable time savings results in the planning of an examination and a simplification of the workflow.

The overview image preferably is assembled from individual images that have at least partially been acquired at different positions of a table on which the examination subject is arranged. For example, a first part of the imaging unit can be acquired at a first table position and the second part of the overview image can be acquired at a second table position. The first part of the overview image can be composed of a number of individual images at the first table position; the second part of the overview image can likewise be composed of a number of images at the second table position. The invention, however, is not limited to the entire overview image being acquired at different table positions. The first part of the overview image thus can be just an individual image or the first part can be formed of a number of individual images. This also applies for the second part of the overview image.

The fact that the overview image is composed of a first part and a second part does not mean that the overview image embodies only two parts; there can also be a number of parts, but there are at least two parts.

In a preferred embodiment, for the acquisition of the first part of the overview image a number of images or slices are acquired at the first table position that are subsequently combined into the first part of the overview image. For acquisition of the second part of the overview image, a number of images or slices can likewise be acquired at the second table position that are combined into the second part of the overview image.

When the first part of the overview image has been provided, this means that the operating personnel already can begin the planning of further measurements in the body region that is shown on the images. Waiting for the last part of the measurement for the overview image is not necessary. As mentioned above, the overview image embodies a first part and a second part. The overview image is naturally not limited to a first part and a second part; the overview image can, for example, also be composed of three parts, for example in a whole-body exposure, wherein the overview image can comprise a head image, an abdomen image and a leg image. According to the invention, the display of the overview image is not delayed until the acquisition of the last part of the overview image; rather, the already-acquired parts of the overview image are provided and displayed immediately after the measurement of the relevant part.

When the position of further images has already been planned based on the first part of the overview image (meaning that the position of the slices in the overview image has been determined), this planned position of the image plane can be transferred to the first part of the overview image upon merging of the first part and the further parts, so the position of the planned image plane is shown on the composite overview image.

Furthermore, the position of images in the first part or the second part of the overview image can be automatically suggested (prompted) by the magnetic resonance system. Given completion of a part of the overview image, the system can suggest slice positions for the further images. The operating personnel can either adopt this position of the images or the position can be modified. The position of the proposed images preferably depends on the anatomical region that is shown in the respective part of the overview image. The user thus receives a planning suggestion from the system for the planning on each of these partial overview images.

DESCRIPTION OF THE DRAWINGS

FIG. 1 is a flowchart of an embodiment for planning an examination according to the invention.

FIG. 2 is a flowchart of a further embodiment for planning an examination according to the invention.

DESCRIPTION OF THE PREFERRED EMBODIMENTS

Figure 3A:
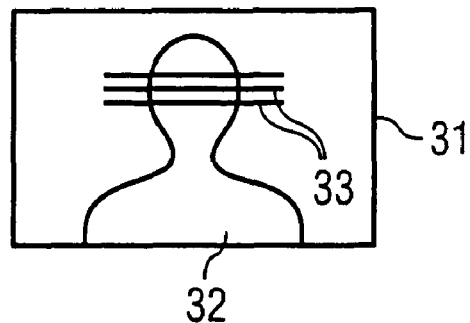
FIGS. 3a through 3c show the partial overview images arising in the planning of the examination according to the invention.

In FIG. 1 steps are shown with which a time savings can be achieved in the planning of an MR examination. In a first step 11, a first part of the overview image is acquired at a first table position, such as by acquiring a number of images of the first body region at the first table position. These images are subsequently assembled to form the first part of the overview image.

This first part of the overview image is then provided (i.e. displayed) to operating personnel in step 12, such that the operating personnel can already begin to plan the actual measurement using this first part of the overview image (step 13). In a step 14, the second part of the overview image is likewise acquired, with another body region being examined (scanned) in this second part at a different table feed position.

In a step 15 the first part and the second part of the overview image are combined, this being implemented with known image processing steps. In a step 16, the composite overview image is then displayed so that the operating personnel can effect further planning based on the composite overview image. In the embodiment shown in FIG. 1, the overview image embodies images that were acquired at two different table positions, whereby each part of the image corresponding to a different table position. Further parts naturally can be added to the overview image, for example a third part that is acquired after a third table feed. According to the invention, however, the first part is displayed before the last part of the overview image has been completely acquired. During the post-processing steps for generation of the first part of the overview image, the acquisition of the second part of the overview image has already begun. It is an important aspect of the invention that the first part of the overview image is displayed before the composite overview image (which can be composed of a number of individual images) can be shown.

A further embodiment is shown in FIG. 2. The head level is acquired at a first table position in a first step 21, meaning that images of the head are acquired at a first table position. In a step 23, the operating personnel can then begin to plan the actual MR examination in the region of the shown head (step 23). For a whole-body acquisition, the abdomen of the examination person is subsequently acquired after a predetermined table feed (step 24), with a number of images, for example, acquired in step 24. The part of the overview image of the head is subsequently combined with the part of the overview image of the abdomen (step 25). When, as is also explained in detail later in connection with FIG. 3, operating personnel have already planned the position of further measurements on the head overview image, the positions of the images planned in the head from step 23 can be adopted in the composite overview image composed of the head and abdomen, such that the head and the abdomen are shown in the representation of the composite image in step 26. The images planned in the head are shown with their respective position in the composite image. The MR examination can now be planned on the composite head and abdomen image.

In a further step 27, the third part of the overview image in which the legs or a part of the legs are shown is finally acquired at a further table position. In a step 28, the part of the overview image of the leg level is added to the previously-combined overview image, whereby a whole-body exposure of the examination person has been acquired that is shown in a step 29. According to the prior art, beginning the planning of the measurement (even on the head) was possible only after step 29 since the overview image was first provided to the user only at that point for planning of further measurements. According to the invention, the individual parts of the overview images are now immediately shown after the acquisition, such that the (in part) time-intensive planning of the further measurements can ensue during the acquisition of the images for the entire overview image. This leads to a significant time reduction in the implementation of examinations, which reduces the total cost of an examination.

Figure 3B:
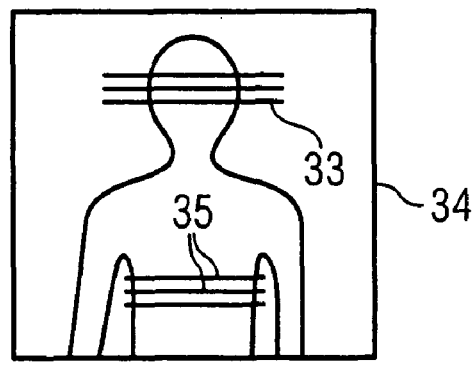
Figure 3C:
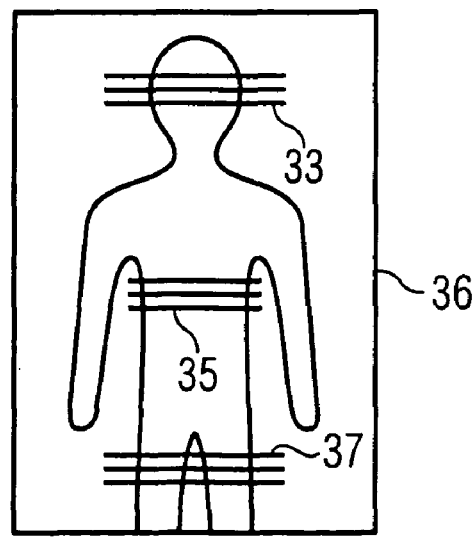

The overview images in the various steps of FIG. 2 are shown in FIG. 3. FIG. 3a shows the first part of the overview image in which primarily the head region of the examined person was acquired. The image shown in FIG. 3a corresponds to the shown image of step 22. After the display, based on a first part 31 of the overview image, the operating personnel can plan slice planes 33 in the examination person images in which should be acquired in the head of the examination subject. The shown slice planning of FIG. 3a can either be automatically suggested by the system for the head and subsequently be modified or adopted by the user, or the user can plan the shown slice planes 33 without a system suggestion.

In FIG. 3, the head and the abdomen of the examination subject are shown in an already-assembled overview image 34, with the abdomen having been measured (scanned) in a second level, and the head part and the abdomen part of the overview image having subsequently been merged into the image 34. The slice planes 33 have been adopted given the display, and the position of further proposed slice planes 35 is furthermore shown by the system using what is known as an auto-align function. This position of the slice planes 35 typically is selected by the system dependent on the examined anatomical region.

Finally, the examination person is shown in a composite overview image 36 in image 3c, with the slice planes 37 being shown in addition to the slice planes 33 and 35 that were adopted from the overview image 34. A suggestion for the positioning of the slice planes 37 is again made by the system.

Those skilled in the art will recognize from the above specification that the present invention enables fast availability of the individual partial overview images, such that the planning of the further examination can begin while the measurement for the subsequently level is still continuing. An automatic adoption of the already-planned slices can likewise ensue based on a new composite overview image such that a significant time savings results in the planning of examinations that are implemented at multiple table positions.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for planning an examination of an examination subject disposed on a table that is movable through a magnetic resonance system, comprising the steps of:
   (a) with said patient table and the examination subject thereon at a first table position in said magnetic resonance system, operating a magnetic resonance system with an examination subject therein to acquire a first part of an overview image of the examination subject;
   (b) operating said magnetic resonance system with the examination subject therein to acquire a second part of said overview image, with the patient table and the examination subject thereon at a second table position, different from said first table position, in said magnetic resonance system;
   (c) making said first part of said overview image available to an operator of the magnetic resonance system before completing acquisition of said second part of said overview image, and at least beginning planning further data acquisition from the examination subject dependent on said first part of said overview image also before completing acquisition of said second part of said overview image;
   (d) combining said first part and said second part into a combination of said first part and said second part of said overview image, that forms at least a portion of said overview image; and
   (e) also making said combination of said first part and said second part of the overview image available to the operator of the magnetic resonance system for planning further data acquisition from the examination subject.

2. A method as claimed in claim 1 wherein step (c) occurs no later than during step (b).

3. A method as claimed in claim 1 wherein step (a) comprises acquiring a plurality of images of the examination subject at said first table position and combining said plurality of images to form said first part of said overview image.

4. A method as claimed in claim 1 wherein step (b) comprises acquiring a plurality of images of the examination subject at said second table position and combining said plurality of images to form said second part of said overview image.

5. A method as claimed in claim 1 comprising completing planning of said position of said images before step (d), to obtain a planned position, and wherein step (d) comprises merging said planned position into said combination of said first part and said second part of the overview image.

6. A method as claimed in claim 1 comprising executing step (c) using a computer having a user interface and in step (c), automatically evaluating said first part of said overview image to automatically generate a suggestion for a position of images of the examination subject in the magnetic resonance system for said planning of said further data acquisition, making said suggestion available to the operator via said user interface, and allowing the operator to confirm or modify the suggestion via said user interface.

7. A method as claimed in claim 1 wherein step (e) comprises automatically evaluating said combination of said first part and said second part of the overview image and automatically suggesting a position of images in the magnetic resonance system for planning said further data acquisition, and making said suggestion available to the operator via said user interface, and allowing the operator to confirm or amend the suggestion via said user interface.

8. A method as claimed in claim 7 comprising, in said computer, automatically generating said suggestion dependent on evaluation of an anatomical region of the examination subject in said combined first part and second part of said overview image.

9. A method as claimed in claim 1 wherein said first part of said overview image and said second part of said overview image are respective parts of N parts forming said overview image, wherein N>2, and comprising acquiring a remainder of said N parts after step (b), and wherein step (d) comprises combining said N parts to form said overview image.

* * * * *